United States Patent [19]

Teng

[11] Patent Number: 4,582,820

[45] Date of Patent: Apr. 15, 1986

[54] ORALLY ADMINISTERED BIOLOGICALLY ACTIVE PEPTIDES AND PROTEINS

[75] Inventor: Lin-nar L. Teng, Bothell, Wash.

[73] Assignee: Research Corporation, New York, N.Y.

[21] Appl. No.: 452,493

[22] Filed: Dec. 23, 1982

[51] Int. Cl.$^4$ .................... A61K 37/26; C07K 7/40
[52] U.S. Cl. ................................ 514/3; 260/112 R; 260/112 T; 260/112.5 R; 260/112.5 TR; 260/112.5 S; 260/112.5 E; 260/112.7; 424/95; 514/2; 514/12
[58] Field of Search .............. 424/25, 178, 177, 329, 424/95; 514/2, 3, 12, 642; 260/112 R, 112 T, 112.5 R, 112.5 TR, 112.5 S, 112.5 E, 112.7

[56] References Cited

U.S. PATENT DOCUMENTS

| | | | |
|---|---|---|---|
| 2,108,765 | 2/1938 | Domagk | 424/329 |
| 2,694,663 | 11/1954 | Stayner | 424/329 |
| 2,844,466 | 7/1958 | Rogers et al. | 424/329 |
| 2,907,693 | 10/1959 | Price et al. | 424/227 |
| 3,869,550 | 3/1975 | Dalgard et al. | 424/329 |
| 4,153,689 | 5/1979 | Hirai et al. | 424/329 |

OTHER PUBLICATIONS

Chemical Abstracts, 89, 1978, Abst. No. 48909t.
Chemical Abstracts, 100(5), 1983, Abst. No. 30577u.
Kubinyi, Arzneim-Forsch/Drug Res., 29(11), No. 8, 1067–1080 (1979).

Primary Examiner—Sam Rosen
Attorney, Agent, or Firm—Scully, Scott, Murphy & Presser

[57] ABSTRACT

An enterally effective, biologically active peptide or protein composition, comprising a sandwich complex comprising a hydrophobic core complex of a biologically active peptide or protein with an alkyl or alkenyl sulfate having 6–24 carbon atoms and 0–3 double bonds which form an electrostatic complex with a soft quaternary ammonium ion of the formula $NR^1R^2R^3R^4$ wherein $R^1$ represents a $C_1$–$C_{12}$-alkyl group; $R^2$ and $R^3$ independently represent hydrogen or a $C_1$–$C_{12}$-alkyl group; and $R^4$ represents hydrogen or a radical of the formula

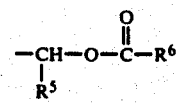

where $R^5$ is hydrogen, $C_1$–$C_5$ n-alkyl group and $R^6$ is a linear alkyl or alkenyl group having 6–22 carbon atoms and 0–3 double bonds; or $R^1$ and $R^2$ together represent a divalent radical of the formula $-CH_2CH_2CH_2CH_2-$, $-CH_2CH_2CH_2CH_2CH_2-$, $-CH=CH-N=CH-$, or $-CH_2CH_2OCH_2CH_2-$ and $R^3$ and $R^4$ have the meanings previously defined; with the proviso that $R^1$, $R^2$ or $R^3$ may optionally be substituted with a hydroxyl group or an alkoxyl group of the formula $-OR^4$ where $R^4$ is an alkyl group having 1–4 carbon atoms; that when $R^1$ and $R^2$ together represent a divalent radical, the radical may be substituted by methyl, hydroxyl, $R^1$, or $-OR^4$; and that when $R^2$ is hydrogen, $R^1$ is not methyl.

36 Claims, No Drawings

ORALLY ADMINISTERED BIOLOGICALLY ACTIVE PEPTIDES AND PROTEINS

BACKGROUND OF THE INVENTION

1. Field of the Invention

The present invention relates to pharmaceutical preparations of biologically active peptides and proteins suitable for enteral administration.

2. Description of the Prior Art

As a result of recent progress in the field of biochemistry, many biologically active peptides and proteins are now available for clinical use. However, because they are proteins of low lipophilicity and can be destroyed in the gastrointestinal tract by enzymes capable of cleaving peptide bonds and in the stomach by acid hydrolysis, methods of administering these compounds orally have not kept pace with their synthesis and identification. Typical of this situation is the case of insulin. It has long been established that insulin is an effective endogenous hormone useful in the treatment of diabetes mellitus. Furthermore, the intact insulin molecule is known to pass through the intestinal wall of various animals under specified conditions. However, adult animals (including humans) absorb insulin poorly when it is orally administered. This is probably due to a combination of factors: destruction of intact insulin molecules as previously discussed and slow passage of intact insulin molecules through the intestinal wall because of low lipophilicity. Consequently, therapeutic use of insulin is limited by the necessity of administering it parenterally, particularly by intravenous or intramuscular injection.

The desire to avoid parenteral administration of insulin has stimulated research efforts in other modes of administration, among which oral administration is the most attractive. Although efforts have been made to develop oral hypoglycemic agents other than insulin, a great deal of effort has also been concentrated on the modification of insulin in such a way that an immunologically intact and metabolically competent insulin molecule can be absorbed through the intestine so that insulin itself or a derivative thereof may be orally administered. The search in this area has been concentrated in three directions: the development of adjuvants, the co-administration of enzymatic inhibitors, and the development of liposomes. Adjuvants used with insulin include resorcinols, non-ionic surfactants such as polyoxyethylene oleyl ether, and n-hexadecyl polyethylene ether. Enzyme inhibitors include pancreatic trypsin inhibitor, diisopropylfluorophosphate (DFP), and trasylol. Liposomes include water-in-oil-in-water insulin emulsions as well as conventional liposomes.

The co-administration of enzyme inhibitors has had some degree of success, particularly when used with duodenal administration. Adjuvants such as hexylresorcinol have been administered with insulin to diabetic patients to give systemic, hypoglycemic effects. However, some adjuvants are limited to successful intra-jejunal administration. Compared to the other types of oral insulin preparations, liposomes have been relative successful. Several studies have shown systemic, hypoglycemic effects after administration of a liposome containing insulin (e.g., Patel et al, FEBS Letters, 62, 60 (1976); Hashimoto et al, Endocrinol., Japan, 26, 337 (1979)). However, liposomes are still in the development stage of their use as oral hypoglycemic agents and face continued problems of stability, shelf-life, and so forth.

The difficulties of preparing other peptide and protein hormones (and other biologically active peptides and proteins) for oral ingestion or other types of enteral administration parallel the problems associated with insulin. Accordingly, there remains a need for a composition generally capable of effecting the oral administration of biologically active peptides and proteins.

SUMMARY OF THE INVENTION

It is an object of the this invention to provide an effective method of orally administering biologically active proteins and peptides.

It is a further object of this invention to provide compositions containing biologically active proteins or peptides which are effective when administered orally or by other enteral methods.

It is still a further object to provide a method of producing such compositions which can be carried out with any biologically active peptide or protein.

These and other objects of the invention as will hereinafter become more readily apparent have been accomplished by providing an enterally effective biologically active peptide or protein composition, comprising:

a sandwich complex comprising a hydrophobic core complex of a biologically active peptide or protein with an alkyl or alkenyl sulfate having 6–24 carbon atoms and 0–3 double bonds which forms an electrostatic complex with a soft quaternary ammonium ion of the formula $NR^1R^2R^3R^4$ wherein $R^1$ represents a $C_1$–$C_{12}$-alkyl group;

$R^2$ and $R^3$ independently represent hydrogen or a $C_1$–$C_{12}$-alkyl group; and $R^4$ represents hydrogen or a radical of the formula

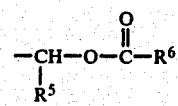

where $R^5$ is hydrogen, $C_1$–$C_5$ n-alkyl group and $R^6$ is a linear alkyl or alkenyl group having 6–22 carbon atoms and 0–3 double bonds; or $R^1$ and $R^2$ together represent a divalent radical of the formula. $-CH_2CH_2CH_2CH_2-$, $-CH_2CH_2CH_2CH_2CH_2-$, $-CH=CH-N=CH-$, or $-CH_2CH_2OCH_2CH_2-$ and $R^3$ and $R^4$ have the meanings previously defined, with the provisos that $R^1$, $R^2$ or $R^3$ may optionally be substituted with a hydroxyl group or an alkoxyl group of the formula $-OR^4$ where $R^4$ is an alkyl group having 1–4 carbon atoms, that when $R^1$ and $R^2$ together represent a divalent radical, said radical may be substituted by hydroxyl, $R^1$, or $-OR^4$, and that when $R^2$ is hydrogen, $R^1$ is not methyl.

DESCRIPTION OF THE PREFERRED EMBODIMENTS

The present invention involves a method of modifying a biologically active protein in such a way that the protein is absorbed into the systemic circulation when administered enterally, particularly orally, while remaining immunologically intact and metabolically competent. To achieve this result, the protein is coupled to a protective carrier in the form of a sandwich complex described in a later section. To be successful in this role, the protein complex must meet the following criteria: (a) it must be resistant to the acidic environment in the stomach; (b) it must be resistant to enzymatic degradation by gastric and pancreatic enzymes; (c) it must be sufficiently lipophilic to pass the intrinsic barrier of the intestinal wall; and finally (d) the changes in physiological and biological properties of insulin molecules resulting from the modification must be minimal so that their hormonal activity is maintained. While criteria (c) and (d) are basic structural requirements for all enterally administered proteins (such as by rectal, buccal or topical routes), criteria (a) and (b) must be met in addition to (c) and (d) for the protein to be orally effective.

More specifically, the present invention provides a sandwich-type complex of a biologically active peptide or protein with an alkyl sulfate and a soft quaternary ammonium ion. The biologically active peptide (hereafter "peptide" or "protein" will refer to both peptide and protein molecules unless otherwise indicated) first forms a hydrophobic core complex with the alkyl sulfate. This core complex protects the peptide molecule from acidic hydrolysis and enzymatic degradation and increases the lipophilicity of the peptide molecule, thereby allowing the intact peptide to pass through the stomach when orally ingested and to increase the rate at which it is absorbed through the intestine wall. This inner complex may be formed between the peptide molecule and the alkyl sulfate. Hydrophobic complexes of a peptide with an alkyl sulfate are generally rod-like with a helical polypeptide chain of the peptide existing within a hydrophobic shell formed by the alkyl sulfate. Typical of alkyl sulfate complexes with protein are those complexes formed with sodium dodecyl sulfate (SDS). SDS has been found to bind protein molecules in constant gram to gram ratios irrespective of nature of protein but depending on the SDS monomer concentration. When SDS monomer concentration exceeds $5 \times 10^{-4}$M, proteins form complexes with SDS in a high binding ratio where one gram of protein binds to about 1.4 gram of SDS. When the SDS monomer is less than $5 \times 10^{-4}$M, proteins form complexes with SDS in a low binding ratio where one gram of, protein binds to about 0.4 gram of SDS. Both protein.SDS complexes assume a similar, rod-like shape with a helical polypeptide chain or protein folded back upon itself near its middle to give a double helical rod and the SDS forming a shell about the rod via hydrophobic forces. The sulfate groups of SDS are on the surface of the rodlike complexes as evidenced by the electrophoretic migration of insulin in the presence or in the absence of SDS. In electrophoresis at pH 3 in the absence of SDS, insulin is fully protonated and migrates to cathode. In the presence of SDS (0.1%) at pH 3, insulin migrates to the anode (as if it is an anion).

Since alkyl sulfates are themselves hydrolyzed to fatty acid alcohols and a sulfuric acid salt at acidities approximately those of the stomach, the rod-like peptide.alkyl sulfate complex requires an additional protective coating for oral administration which is provided by a soft quaternary ammonium ion, the structures of which are described later in detail.

By utilizing the method of the invention, it is possible to prepare peptide compositions suitable for oral administration which contain endogenous opioid agonists, such as encephalins and endorphins; hypothalmic hormones, such as gonadoliberin, melanostatin, melanoliberin, somatostatin, thyroliberin, substance P, and neurotensin; adenohypophyseal hormones, such as corticotropin, lipotropin, melanotropin, lutropin, thyrotropin, prolactin, and somatotropin; neurohypophyseal hormones; calcitropic (thyroid) hormones, such as parathyrin and calcitonin; thymic factors, such as thymosin, thymopoietin, circulating thymic factor, and thymic humoral factor; pancreatic hormones, such insulin, glucagon, and somatostatin; gastrointestinal hormones, such as gastrin, cholecystokinin, secretin, gastric inhibitory polypeptide, vasointestinal peptide, and motillin; chorionic (placental) hormones, such as choriogonadotropin and choriomammotropin; ovarian hormones, such as relaxin; vasoactive tissue hormones, such as angiotensin and brandykinin; growth factors, such as somatomedins, epidermal growth factor, urogastrone, and nerve growth factor; hemophilia factors, such as blood clotting factors VIII and IX; enzymes, such as streptokinase, fibrinolysin, deoxyribonuclease, and asparaginase; and artificial or pseudo peptides, such as deferoxamine. Many other classes and specific types of peptide and protein hormones and other biologically active molecules are known. Peptide and protein hormones suitable for use in the present invention are disclosed in Johannes Meienhofer, "Peptide and Protein Hormones", in *Burger's Medicinal Chemistry*, 4th ed., (part II), Wolff, Ed., John Wiley and Sons (1979), which is herein incorporated by reference. Preferred hormones are those with a molecular weight of less than 7000, with insulin being especially preferred.

The listings of peptides and proteins in this application are not intended to be exclusive, and it may easily be determined by simple experimentation if any Protein having biological activity can be prepared into a complex according to the invention. One simple method of testing for core complex formation involves the following steps: (1) dissolve approximately 10 mg of the biologically active peptide or protein in a small amount of water or buffer; (2) adds about 15 mg of an alkyl sulfate, for example sodium dedecyl sulfate, mix well and allow to stand for about 5 minutes; (3) subject the resulting solution to agarose or acrylamide gel electrophoresis. The complex acts as an anion even at low pH (about 3 is a good testing point) because of the sulfate groups and migrates toward the anode. If no complex has formed, the protein will be protonated at low pH and migrate toward the cathode.

If complex formation has taken place and if the resulting core complex will itself complex with a soft quaternary ammonium ion according to the process of the present invention (infra), the biologically active peptide is suitable for use in the present invention.

Complex formation between protein and a carrier molecule is one way to protect a protein molecule from acidic hydrolysis and enzymatic degradation and to increase the lipophilicity of the protein molecule. Depending on the carrier substances selected, formation of this complex can be via columbic interaction between protein molecule and carrier substance or via hydrophobic forces. In the proposed sandwich complex of protein:alkyl sulfate.soft quaternary ammonium ion, there is a "core" complex of protein and alkyl sulfate formed via hydrophobic forces, and there is electrostatic attraction between the sulfate groups of the alkyl sulfate and the soft quaternary ammonium ions.

Unlike other chemical modifications, complex formation between an agent and a carrier substance is a molecular modification of the agent without any chemical alteration of the molecule itself. It is a method of modification in which the biological integrity of the molecule remain more or less intact. This is especially true in complexes formed via columbic forces.

Alkyl sulfates useful in the present invention have linear, branched, or cyclic alkyl groups having 6–24 carbon atoms. Of these, linear alkyl groups, preferably with 8–18 carbon atoms, are preferred, especially those having an even number of carbon atoms. Alkenyl sulfates having 1–3 double bonds are also suitable. Specific examples of suitable alkyl and alkenyl sulftaes include octyl, decyl, dodecyl, tetradecyl, hexadecyl, octadecyl, 10-methyloctadecyl, 4-hexylcyclohexyl, 9-octadecenyl, 9,12-octadecadienyl, 9,12,15-octadecatrienyl, and tetracosyl sulfate.

Sulfates of the invention can be synthesized by standard methods of synthesis using alcohols (e.g., fatty alcohols) and sulfuric acid or sulfate salts. Many alkyl sulfates, e.g., sodium dodecyl sulfate, are commercially available. Suitable examples of preferred linear alkyl sulfates include octyl sulfate, nonyl sulfate, decyl sulfate, undecyl sulfate, dodecyl sulfate, tridecyl sulfate, tetradecyl sulfate, pentadecyl sulfate, and hexyl sulfate. Of these, decyl sulfate, dodecyl sulfate and tetradecyl sulfate are more preferred with dodecyl sulfate being most preferred.

The alkyl sulfates are generally present initially as alkali metal salts when the initial core complex is being formed. Alkali metal salts include lithium, sodium, potassium, rubidium and cesium salts. Of these, sodium and potassium are preferred, with sodium salts being most preferred. Sodium and potassium salts of dodecyl sulfate are especially preferred, with sodium dodecyl sulfate being the most preferred alkyl sulfate salt.

The weight ratio of protein or peptide to alkyl sulfate is the weight ratio of the naturally forming complex. In a preferred embodiment, insulin is complexed with sodium dodecyl sulfate (SDS). This complex forms an insulin:SDS complex in a ratio of 1:1.4 or 1:0.4 by weight (depending on the initial ratio present) and is a hydrophobic complex. Complexes of protein with SDS are preferred to other types of complexes because a wide variety of proteins are reported to bind to an identical amount of SDS on a gram per gram basis. See, for example, Reynolds et al., *Proc. Nat. Acad. Sci. (US)*, 66, 1002–1003 (1970) and Reynolds et al., *J. Biol. Chem.*, 245, 5161–5165 (1970). When SDS forms a complex with insulin or other protein, the hydrophobic core complex is rod-like with a helical polypeptide chain of protein existing within a hydrophobic shell formed by the SDS. This complex of protein with alkyl sulfate is referred to herein as a core complex. This term is not intended to limit the present invention, but is believed to be generally descriptive. When this core complex is itself complexed with a soft quaternary ammonium ion, an additional layer forms on the surface of the inner complex. This latter complex is referred to as an "electrostatic" complex. Nevertheless, this term additionally is not intended to be limiting of the actual physical structure that is present in the resulting complex.

As mentioned above, the inner complex is reacted with a soft quaternary ammonium ion to form an outer complex. The phrase "soft quaternary ammonium ion" as used in this invention includes protonated organic amines and other amine derivatives as will later be defined. A suitable amine from which to form a protonated amine of the invention has the formula $NR^1R^2R^3$ wherein $R^1$ represents a $C_1$–$C_{12}$-alkyl group and wherein $R^2$ and $R^3$ independently represent hydrogen or a $C_1$–$C_{12}$-alkyl group. Representative alkyl groups include methyl, ethyl, propyl, isopropyl, butyl, isobutyl, sec-butyl, pentyl, neopentyl hexyl, heptyl, octyl, nonyl, decyl, undecyl, and dodecyl. Additionally, $R^1$ and $R^2$ together can represent a divalent alkylene radical which, when taken together with the amine nitrogen, forms a 5- or 6-membered ring. Examples of suitable radicals include $-CH_2CH_2CH_2CH_2-$, $-CH_2CH_2CH_2CH_2CH_2-$ and derivatives of these radicals having an alkyl group of formula $R^1$ in place of one or two hydrogen atoms of said radical. Furthermore, $R^1$ and $R^2$ when taken together with the amine nitrogen may form an imidazole or morpholine having the formula

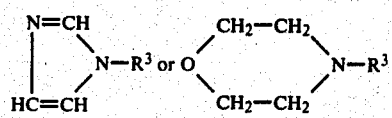

Additionally, any of the substituents $R^1$–$R^3$ previously defined may be substituted with a hydroxyl or alkoxyl group, wherein the alkoxyl group has the formula $-OR^4$ where $R^4$ is an alkyl group having 1–4 carbon atoms. It is preferred that the amine contain a total of 3–15 carbon atoms with 6–10 carbon atoma being more preferred. Specific examples of suitable amines include trimethylamine, triethylamine, n-propylamine, methyldiethylamine, diethylamine, methylbisethoxyethylamine, methyl-4-hydroxybutylpentylamine, N-methylpyrrolidine, N-ethylimidazole, and morpholine. Preferred amines include trimethylamine, triethylamine, tripropylamine, morpholine, N-alkylimidazoles, and N-alkylpyrrolidines. The amines used in this invention are readily available either commercially or through standard methods of synthesis. Methylamine and dimethylamine should specifically be avoided because of the carcinogenic products formed when they react with nitrites under acidic conditions (e.g., in the stomach).

When the amines of the invention are formulated into the outer complex, they are present as protonated amines. Preferred are amines protonated with mineral acids such as, for example, sulfuric acid and hydrochloric acid. However, organic acid salts, such as salts of oxalic or lactic acid, may also be used. Amine hydrochlorides are especially preferred.

In addition to protonated amines, other soft quaternary ammonium ions may also be used to form the electrostatic complex of the invention. By soft quaternary ammonium ion is meant an ion of the formula

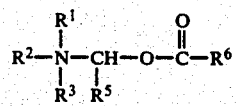

where $R^1$–$R^3$ have the meanings previously given, $R^5$ is hydrogen, methyl or ethyl, and $R^6$ is the alkyl or alkenyl residue of a naturally occurring fatty acid of formula $R^6CO_2H$. $R^6$ may additionally be any linear alkyl group having 6–22 carbon atoms or any linear alkenyl group having 6–22 carbon atoms and 1–3 double bonds. Other quaternary ammonium ions which hydrolyze or are otherwise cleaved to release harmless organic compounds are contemplated as equivalents. The principal requirement of a soft quaternary ammonium ion is the ability to lose its positive charge in a biological system by deprotonation, hydrolysis, or enzymatic degradation.

In the acidic environment of the stomach, a soft quaternary ammonium ion of the previously given formula in a sandwich complex will hydrolyze to give a fatty acid, an aldehyde and a (protonated) substituted ammonium ion and leave an unprotected "core" complex of protein:alkyl sulfate. Depending on the rates of hydrolysis of the sulfate to an alcohol and acid sodium sulfate and of the protein itself, an electrostatic complex may form between the "core" complex and the protonated substituted ammonium ion generated in situ. In other words the soft quaternary ammonium ion of the given formula is designed here not only for its added lipophilicity due to the presence of the ester moiety, but also so that once it is hydrolyzed in an acidic environment, another "soft" quaternary ammonium ion, in this case, a protonated amine, takes its place to provide continued protection for the hydrophobic "core" complex.

The synthesis of a soft quaternary ammonium ion involves two steps, the preparation of an α-chloroalkyl ester, and the formation of the desired quaternary ammonium ion:

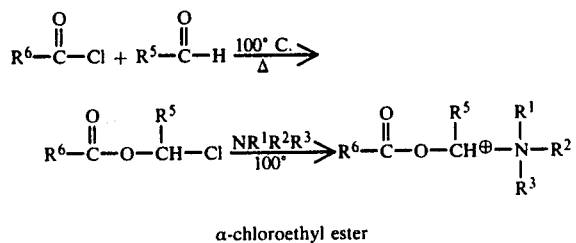

α-chloroethyl ester

Since a soft quaternary ammonium ion is a positively charged reagent and since the alkyl sulfate is a negatively charged reagent, a 1:1 molar ratio of the soft quaternary ammonium ion with the alkyl sulfate is preferred. However, other ratios are possible and fall within the scope of the invention. Ratios of amine to alkyl sulfate in the range from 1:0.3 to 1:1 are contemplated by the present invention. Such ratios are obtained by using an excess of the core complex or the amine/ammonium ion component during formation of the electrostatic complex.

The final electrostatic complex is formed by adding the soft quaternary ammonium ion to an aqueous solution containing a protein.alkyl sulfate complex (i.e., the core complex). The resulting electrostatic complex comprising the entire protein.alkyl sulfate.soft quaternary ammonium ion complex can be isolated by extracting the aqueous solution with chloroform or another non-polar solvent immiscible with water. The presence of protein in the extracted complex can be verified using the Fluorescamine protein test as described in Udenfried et al, *Science*, 178, 871–872 (1972), which is herein incorporated by reference. When working with a previously untried complex, this allows easy verification of the formation of the desired complex.

This invention may be carried out either by preparing a pharmaceutical composition which may be stored in that form or by producing the sandwich complex immediately prior to administration. When a protonated amine is used to form the final complex, the complex can be stored at approximately 4° C. in 0.005 M phosphoric acid for at least 2 weeks. When a soft quaternary ammonium ion is used, the complex should be prepared in deionized water at a pH of approximately 7. It can then be lyophilized and stored in powder form for at least several months. Since oral administration is the principal contemplated end use of the compositions of the present invention, compositions suitable for oral ingestion are preferred storage forms. Such compositions can contain pharmaceutically acceptable carriers in addition to the previously disclosed ingredients. Suitable pharmaceutical carriers include liquid or solid carriers of pharmaceutically acceptable or otherwise inert materials which may be used orally. Examples of liquids are water and aqueous solutions of non-toxic salts, such as sterile physiological solutions of saline, or aqueous solutions containing non-toxic organic solvents, such as ethanol, used to increase the amount of complex in solution. Dilute aqueous solutions of mineral acids having a pH of less than 4 are also suitable. Phosphoric, sulfuric, and hydrochloric acids are preferred. Also suitable are emulsions, such as oil-in-water emulsions. Solutions of non-toxic organic liquids, such as ethanol, are also suitable. Solid carriers include both nutritive carriers, such as sucrose or gelatin, and non-nutritive carriers, such as cellulose or talc. A pharmaceutical preparation of the invention may be in the form, for example, of a liquid, a capsule, a tablet, or a suppository.

Pharmaceutical compositions according to the present invention are administered in dosages which depend upon the effect desired for the biologically active compound which is being administered. The determination of the effective amount of the biological compound is not considered to be part of the present invention since dosage rates are generally determined by the effect of the composition on the particular patient taking the medication. An amount equal in dose rate (mg/kg) to the amount normally injected parenterally for known biologically active peptides is suitable for use in the present invention as an initial dose and may be adjusted as necessary to achieve the desired effect.

A particularly preferred embodiment of this invention comprises enterally administering a sandwich complex of the invention containing insulin as the active ingredient to produce a hypoglycemic effect. The amount required will depend on the severity of the diabetes and on the condition of the patient (e.g., time since ingestion of food, type and amount of food ingested, etc.). Adjustment of the amount required to maintain the proper blood glucose level is within the capability of those of ordinary skill in the art. An orally administered sandwich complex (of insulin or any other active peptide) is especially preferred.

The above disclosure generally describes the present invention. A more complete understanding can be obtained by reference to the following specific examples which are provided herein for purposes of illustration only and are not intended to be limiting unless otherwise specified.

EXAMPLE 1

An insulin sandwich complex comprising insulin:sodium dodecyl sulfate:triethylamine hydrochloride in a weight ratio of 5:7.5:3.6 was prepared. Insulin (bovine pancreas, crystalline; 25.5 μ/mg; Sigma; 10 mg total) was dissolved in a small amount of 0.005 M H$_3$PO$_4$, pH 2.45, in a 5 ml volumetric flask. Sodium dodecyl sulfate (15 mg) was added and mixed well to give a clear solution. After the solution was allowed to stand for 5 minutes, 7.2 mg of triethylamine hyrochloride was added. The volumetric flask was then filled to 5.0 ml with 0.005

M $H_3PO_4$, pH 2.45 to give the final insulin:SDS:TEA complex.

EXAMPLE 2

In Vivo Tests of Sandwich Complex

The term "diabetic rat" in the following tests refers to rats having been treated with streptozoticin by intravenous injection at a dosage of 75 mg/kg at least 4 days prior to the experiments in question. All rats used in the experiments had been fasting 12–18 hours prior to the experiments. Blood samples were taken at appropriate intervals as disclosed in the tables from a vein cannula which was implanted in a jugular vein. During the experiments, rats were awake, were able to move freely and had access to water (but no food). Plasma glucose was measured on a Beckman Glucose Analyzer 2 employing the enzymatic reaction of $\beta$-D-glucose with oxygen and measuring oxygen consumption rather than hydrogen peroxide formation.

A. Intravenous (iv) Administration of Regular and Modified Insulin in Diabetic Rats The results of iv administration of regular and modified insulin in diabetic rats are shown in Tables 1 and 2 respectively. Both regular and modified insulin yielded progressive, systemic, hypoglycemic effects for five hours in all animals. From 15 min to 45 min after iv administration, the induced hypoglycemic effect was more pronounced in regular-insulin-treated animals. Then from 60 min to 2 hrs after iv administration, the hypoglycemic effects among regular- and modified-insulin-treated rats became comparable. After 2 hours, the blood glucose level in the modified-insulin-treated rats returned to the initial level faster than in the regular-insulin-treated rats; e.g., five hours after administration, in the modified insulin group 89.1% of the initial plasma glucose concentration was observed while in the regular insulin group 65.7% of the initial plasma glucose concentration was found.

Among the individual rats treated with both agents, rat #285 showed a progressive hypoglycemic effect after iv administration of regular insulin (4th row in Table 1), whereas iv administration of insulin:SDS:-TEA complex only yielded a slight hypoglycemic effect (Table 2, 3rd row). On the other hand, rat #3 showed more pronounced hypoglycemic effect for the first 90 min when the rat was treated with the insulin complex than when it was treated with regular insulin whereas the reverse was true in the later hours (see 5th row in Table 2 vs 6th row in Table 1).

The data do indicate that insulin in a sandwich complex of insulin SDS TEA with a weight ratio of 5:7.5:3.6 remains physiologically effective. Compared with the hypoglycemic effect of regular insulin in diabetic rats, the hypoglycemic effect of the modified insulin is not as sustaining. In all likelihood, the presence of a protein denaturing agent, SDS, in the sandwich complex probably reduces the physiological effectiveness of insulin to a certain extent.

TABLE 1

Intravenous Administration of Insulin (0.5 μ/kg) Into Diabetic Rats

% Initial plasma glucose conc: (Actual 277.9 Glucose mg %) At Time Intervals After Administration

| Rat No. | Bd. Wt. (g) | 0 | 15 min | 30 min | 45 min | 60 min | 90 min | 120 min | 180 min | 300 min |
|---|---|---|---|---|---|---|---|---|---|---|
| 4 | 312.5 | 100 | 46.1 | 43.9 | 36.5 | 38.4 | 45.4 | 42.3 | 58.8 | 60.8 |
|  |  | (362) | (197) | (159) | (132) | (139) | (168) | (153) | (213) | (220) |
| 8 | 300.5 | 100 | 63.8 | 53.6 | 59.1 | 57.6 | 53.6 | 58.0 | 59.8 | 58.1 |
|  |  | (276) | (176) | (148) | (163) | (159) | (148) | (160) | (165) | (167) |
| 10 | 274.5 | 100 | 57.7 | 16.2 | 31.0 | 27.2 | 50.4 | 56.9 | 76.3 | 89.2 |
|  |  | (371) | (214) | (60) | (84) | (101) | (187) | (211) | (283) | (331) |
| 285 | 230 | 100 | 84.5 | 69.7 | 56.2 | 51.8 | 46.1 | 35.1 | 37.9 | 46.6 |
|  |  | (425) | (359) | (296) | (239) | (220) | (196) | (149) | (161) | (198) |
| 1 | 290 | 100 | 47.9 | 36.9 | 41.5 | 48.3 | 51.7 | 60.6 | 67.8 | 90.7 |
|  |  | (236) | (113) | (87) | (98) | (114) | (122) | (143) | (160) | (214) |
| 3 | 260 | 100 | 82.5 | 79.4 | 65.3 | 71.6 | 70.7 | 47.8 | 45.9 | 48.6 |
|  |  | (451) | (372) | (358) | (296) | (323) | (319) | (215) | (207) | (219) |
| Mean ± Stand. Deviat. | 277.9 ± 29.9 | 100 (339 ± 85) | 63.8 ± 16.6 (239 ± 104) | 50.0 ± 22.9 (185 ± 118) | 48.3 ± 13.8 (169 ± 83) | 49.2 ± 15.4 (176 ± 83) | 53.0 ± 9 (190 ± 69) | 50.1 ± 10.1 (177 ± 32) | 57.8 ± 14.0 (196 ± 48) | 65.7 ± 19.6 (225 ± 56) |

TABLE 2

Intravenous Administration of Insulin Complex Into Diabetic Rats (0.5 μ/kg)

% Initial plasma glucose Conc. (Actual plasma glucose conc. in mg %) at designated time interval

| Rat # | Bd. Wt. (g) | 0 | 15 min | 30 min | 45 min | 60 min | 90 min | 120 min | 180 min | 300 min |
|---|---|---|---|---|---|---|---|---|---|---|
| 283 | 272 | 100 | 76.7 | 69.7 | 60.1 | 53.6 |  | 51.4 | 64.1 | 76.5 |
|  |  | (446) | (342) | (311) | (269) | (239) |  | (229) | (286) | (341) |
| 284 | 289 | 100 | 68.4 | 69.8 | 71.5 | 53.0 | 43.9 | 43.0 | 68.7 |  |
|  |  | (421) | (288) | (294) | (301) | (223) | (195) | (181) | (289) |  |
| 285 | 249 | 100 | 110 | 77.0 | 79.8 | 72.9 | 103.7 | 70.7 | 97.8 | 94.7 |
|  |  | (321) | (356) | (247) | (256) | (234) | (333) | (277) | (314) | (304) |
| 286 | 337.5 | 100 | 52.7 | 68.2 | 60.5 | 58.9 | 24.0 | —* | —* | —* |
|  |  | (129) | (68) | (88) | (78) | (76) | (31) |  |  |  |
| 3 | 263 | 100 | 39.3 | 63.8 | 51.5 | 57.1 | 60.1 | 63.8 | 74.2 | 87.1 |
|  |  | (163) | (64) | (104) | (84) | (93) | (98) | (104) | (121) | (142) |
| 9 | 283 | 100 | 72.9 | 47.4 | 53.4 | 44.7 | 57.9 | 53.7 | 79.7 | 97.9 |
|  |  | (383) | (277) | (180) | (203) | (170) | (220) | (204) | (303) | (372) |
|  | 282.3 ± 30.6 | 100 (311 ± 135) | 70.0 ± 24.1 (233 ± | 66.0 ± 10.1 (204 ± | 62.8 ± 10.9 (199 ± | 56.7 ± 9.3 (173 ± 73) | 57.9 ± 29.4 (175 ± 116) | 56.5 ± 10.9 (199 ± | 76.9 ± 13.1 (263 ± | 89.1 ± 9.5 (290 ± |

TABLE 2-continued

| | Bd. Wt. | Intravenous Administration of Insulin Complex Into Diabetic Rats (0.5 μ/kg) | | | | | | | | |
|---|---|---|---|---|---|---|---|---|---|---|
| | | % Initial plasma glucose Conc. (Actual plasma glucose conc. in mg %) at designated time interval | | | | | | | | |
| Rat # | (g) | 0 | 15 min | 30 min | 45 min | 60 min | 90 min | 120 min | 180 min | 300 min |
| | | | 132) | 95) | 96) | | | 64.0) | 80) | 102) |

*Died of convulsion

B. Oral Administration of Regular and Modified Insulin (at 80μ/kg) in Normal and Diabetic Rats.

In order to prove that the systemic hypoglycemic effect observed after oral administration of insulin:SDS:TEA in diabetic (or normal) rats, if any, is due to the complex per se and not due to the presence of SDS:TEA nor to nonspecific protein:SDS:TEA complexes, oral administration of insulin:SDS:TEA in diabetic rats were run against three controls. The three controls were regular insulin, a carrier complex of SDS:TEA, and a complex of albumin:SDS:TEA in the same weight ratio as than in the insulin complex; i.e., albumin:SDS:TEA = 5:7.5:3.6.

The results of oral administrations of modified insulin and carrier complex (SDS:TEA = 1:1 by mole) in the amount equivalent to that in the sandwich complex of insulin calculated based on 80μ of insulin per kg of rat in normal rats are shown in Tables 3 and 4. The results of oral administrations of modified insulin, regular insulin, carrier complex and the sandwich complex of albumin (albumin:SDS:TEA in a weight ratio of 5:7.5:3.6) in diabetic rats are shown in Tables 5, 6, 7 and 8 respectively.

As shown in Tables 3 and 5, oral administration of modified insulin in both diabetic and normal rats give a systemic, hypoglycemic effect in rats which lasts at least five hours. The streptozotocin treated rats respond to modified insulin to a much greater extent than do normal rats; i.e., the glucose level is about 20% lower (compare Tables 3 and 5).

In contrast, the oral administration of regular insulin does not result in a systemic, hypoglycemic effect in diabetic rats (see Table 6). The same conclusion can be drawn from other control studies. Oral administration of the electrostatic complex of SDS:TEA does not yield a systemic, hypoglycemic effect in normal (see Table 4) and diabetic (see Table 7) rats. Nor does the oral administration in diabetic rats of a sandwich complex of a protein which does not have hypoglycemic effect per se. Likewise, the oral administration of a sandwich complex of albumin:SDS:TEA in the weight ratio of 5:7.5:3.6 in diabetic rats fails to produce a systemic hypoglycemic effect.

The experimental results reflected in the above data show that by forming a complex with a lipophilic substance like TEA in the form of a sandwich complex of insulin:SDS:TEA, the lipophilicity of insulin is improved. By doing do, metabolically competent insulin molecules are able to pass through the lipid barrier of the gastrointestinal tract and thence into the circulation to produce a progressive, systemic hypoglycemic effect in normal and diabetic rats.

TABLE 3

| | | Oral Administration of Modified Insulin in Normal Rats (80 μ/kg) | | | | | | | |
|---|---|---|---|---|---|---|---|---|---|
| | | | Glucose Level (% initial level) at Time Interval After Administration (min.) | | | | | | |
| # Rat | Bd. Wt. (g) | 0 (Initial Glucose mg/100 ml) | 15 | 30 | 45 | 60 | 120 | 180 | 300 |
| 211 | 486.9 | 100(134) | 67.9 (91) | 64.2 (86) | 76.9 (103) | 73.2 (98) | 88.8 (119) | 85.1 (114) | 57.5 (77) |
| 212 | 507 | 100(116) | 99.1 (115) | 97.4 (113) | 69.8 (81) | 106.9 (124) | — | 87.1 (101) | 89.7 (104) |
| 214 | 455 | 100(171) | 72.8 (133) | 88.9 (152) | 108.8 (186) | 26.9 (46) | 43.9 (75) | 68.4 (117) | 77.2 (132) |
| 215 | 537.6 | 100(95) | 56.8 (54) | 50.5 (48) | 49.5 (47) | 49.5 (47) | 84.2 (80) | 115.8 (110) | 131.6 (125) |
| 230 | 411 | 100(123) | — | 72.4 (89) | — | 92.7 (114) | 74.0 (91) | 91.1 (112) | 85.4 (105) |
| 231 | 410 | 100(90) | — | 107.8 (97) | — | 108.9 (98) | 92.2 (83) | 95.6 (86) | 107.8 (98) |
| Mean ± Std. Dev. | | 100 (122 ± 29) | 74.1 ± 18.2 (122 ± 51) | 80.0 ± 21.7 (98 ± 34) | 78.1 ± 25.0 (104 ± 59) | 76.3 ± 33.4 (87 ± 26) | 76.6 ± 19.5 (90 ± 17) | 90.6 ± 15.4 (107 ± 11) | 91.5 ± 25.6 (107 ± 20) |

TABLE 4

| | | Oral Administration of Carrier Complex In Normal Rats | | | | | | | |
|---|---|---|---|---|---|---|---|---|---|
| | | (The amount of carrier complex is equal to that in complex insulin · SDS · TEA at 80 μ/kg but without insulin) | | | | | | | |
| | | % Initial plasma Glucose conc. (actual Plasma glucose mg/100 ml) at Time Interval After Administration (min) | | | | | | | |
| Rat | Bd. Wt. (g) | Glucose mg/100 ml | 15 | 30 | 45 | 60 | 120 | 180 | 300 |
| 42 | 474 | 100(80) | 157.5(126) | 142.5(114) | 175(140) | 152.5(122) | 156.3(125) | 152.5(122) | 141.3(113) |
| 43 | 415 | 100(129) | 124(160) | 132.6(171) | 128.7(166) | 131.0(169) | 127.1(164) | 101.6(131) | 77.5(100) |
| 45 | 445 | 100(106) | 129.3(137) | 117.9(125) | 105.1(122) | 84.9(90) | 102.8(109) | 90.6(96) | —* |
| 46 | 476 | 100(110) | 125.5(138) | 115.5(127) | 105.5(116) | 101.8(112) | 90.0(99) | 91.8(101) | —* |
| 47 | 553 | 100(128) | 121.6(186) | 119.5(153) | 115.6(148) | 110.9(142) | 98.4(126) | 106.3(136) | —* |
| 48 | 461 | 100(124) | 124.2(154) | 105.7(131) | 100(124) | 102.4(127) | 100(124) | 92.7(115) | —* |
| Mean ± Std. | 470.1 ± 46.2 | 100(113 ± 18.7) | 130.4 ± 13.4 (150 ± 21) | 122.3 ± 13.2 (137 ± 21) | 121.7 ± 28.1 (136 ± 9) | 113.9 ± 24.1 (127 ± 27) | 112.4 ± 24.9 (125 ± 22) | 105.9 ± 23.7 | 109.4 ± 45.1 |

TABLE 4-continued

Oral Administration of Carrier Complex In Normal Rats
(The amount of carrier complex is equal to that in complex insulin · SDS · TEA at 80 µ/kg but without insulin)

% Initial plasma Glucose conc. (actual Plasma glucose mg/100 ml) at Time Interval After Administration (min)

| Rat | Bd. Wt. (g) | Glucose mg/100 ml | 15 | 30 | 45 | 60 | 120 | 180 | 300 |
|---|---|---|---|---|---|---|---|---|---|
| Dev. | | | | | | | | (117 ± 16) | (107 ± 9) |

*Plasma samples were not stored in the Freezer (−20° C.), but left at room temperature for three days

TABLE 5

Oral Administration of Modified Insulin to Diabetic (Streptozotocin-treated) Rats (80 µ/kg)

Glucose Level (% initial level) at Time Interval After Administration

| # Rat | Bd. Wt. (g) | 0 (Initial Glucose mg/100 ml) | 15 | 30 | 45 | 60 | 120 | 180 | 300 |
|---|---|---|---|---|---|---|---|---|---|
| 220 | 496 | 100(133) | 60.2 (82) | 40.6 (54) | — | 37.1 (49) | 31.6 (42) | 27.6 (37) | — |
| 222 | 425 | 100(108) | 123.6 (140) | 106.9 (137) | 119.4 (129) | 72.2 (78) | 79.6 (86) | 87.0 (94) | 80.6 (87) |
| 226 | 379 | 100(298) | 88.6 (264) | 38.3 (114) | 36.9 (110) | 29.2 (87) | 21.1 (63) | 23.2 (69) | 29.5 (88) |
| 227 | 424.5 | 100(124) | 62.1 (77) | 44.4 (55) | 50.8 (63) | 35.5 (44) | 46.8 (58) | 55.5 (70) | 83.1 (103) |
| 218 | 441 | 100(292) | 69.9 (204) | 37.3 (109) | 32.5 (95) | 21.6 (63) | 12.0 (35) | 16.1 (47) | 44.9 (131) |
| 219 | 519 | 100(166) | 98.2 (163) | 77.1 (128) | 72.3 (120) | 75.9 (126) | 73.7 (122) | 68.7 (114) | 71.1 (118) |
| Mean ± Std. Dev. | | 100 (187 ± 86) | 75.8 ± 16.8 (155 ± 72) | 57.4 ± 28.1 (100 ± 36) | 62.4 ± 35.5 (103 ± 26) | 45.3 ± 23.0 (75 ± 30) | 44.1 ± 27.8 (68 ± 32) | 38.2 ± 22.7 (72 ± 29) | 61.8 ± 23.6 (105 ± 19) |

TABLE 6

Oral Administration of Unmodified Insulin to Diabetic (Streptozotocin-treated) Rats (80 µ/kg).

Glucose Level (% initial level) at Time Interval After Administration

| # Rat | Bd. Wt. (g) | 0 (Initial Glucose mg/100 ml) | 15 | 30 | 45 | 60 | 120 | 180 | 300 |
|---|---|---|---|---|---|---|---|---|---|
| 222 | 415.5 | 100(122) | 119 (145) | — | — | 124.6 (152) | 100 (122) | — | — |
| 226 | 367 | 100(237) | 155.2 (371) | 122.6 (293) | 113.0 (270) | 129.3 (309) | 120.5 (288) | 123.9 (296) | 121.3 (290) |
| 218 | 364 | 100(351) | — | — | — | 77.5*[1] (272) | 71.5*[1] (251) | 64.5*[1] (226) | 53.8*[1] (189) |
| 219 | 496 | 100(146) | 146.6 (214) | — | — | 225.3 (329) | 268.5 (392) | 243.8 (502) | 234.2 (342) |
| 228 | 374.5 | 100(318) | 115 (363) | 107.9 (343) | 132.4 (421) | 128.9 (410) | 129.2 (411) | 132.7 (422) | 123.0 (391) |
| 229 | 386.3 | 100(407) | — | 83.5*[2] (340) | 71.3*[2] (290) | 58.7*[2] (239) | 38.6*[2] (157) | 51.8*[2] (211) | 48.2*[2] (196) |
| Mean ± Std. Dev. | | 100(264 ± 115) | 134 ± 20 (273 ± 112) | 104.7 ± 19.8 (325 ± 28) | 105.6 ± 31.2 (327 ± 82) | 124.1 ± 57.9 (285 ± 87) | 121.4 ± 79.4 (270 ± 118) | 123.3 ± 76.1 (331 ± 127) | 116.1 ± 75.0 (282 ± 89) |

*[1] Blood sample was taken under stress condition-jugular cannula did not work. Every sample was withdrawn from the tail artery when the rat was under ether anesthization.
*[2] Insulin solution (1.10 ml of 1.1 mg insulin/1 ml 0.005M $H_3PO_4$, pH 2.45) was probably administered into the respiratory system of the rat instead of the stomach. Rat looked rather sick for 30 min. after administration.

TABLE 7

Oral Administration of Carrier Complex in Diabetic (Streptozotocin Treated) Rats. (The amount of carrier complex is equal to that in complex insulin · SDS · TEA at 30 µ/kg without insulin.)

Glucose Level (% initial level) at Time Interval After Administration (min)

| # Rat | Bd. Wt. (g) | 0 (Initial Glucose mg/100 ml) | 15 | 30 | 45 | 60 | 90 | 120 | 180 | 300 |
|---|---|---|---|---|---|---|---|---|---|---|
| 251 | 440 | 100(91) | 128.6(117) | 102.2(93) | 106.6(97) | 103.3(94) | 100(91) | 103.3(94) | 100(91) | 103.3(94) |
| 253 | 456 | 100(97) | 117.5(114) | 106.2(103) | 101(98) | 78.4(76) | 82.5(80) | 99.0(96) | 129.9(126) | 106.2(103) |
| 256 | 497.5 | 100(84) | 127.4(107) | 148.8(125) | 154.7(130) | 158.3(133) | 156(131) | 163(137) | 126.2(106) | 91.7(77) |
| 257 | 553.5 | 100(94) | 116(109) | 117.7(105) | 98.9(93) | 116(105) | 93.6(88) | 87.2(82) | 69.2(65) | 103.2(97) |
| 272 | 340.0 | 100(403) | 100.3(404) | 115.6(466) | 100(403) | 109(441) | 118.9(449) | 108.9(439) | 123.6(498) | 99.8(402) |
| 273 | 324 | 100(341) | 101.2(343) | 103(354) | 101.8(347) | 87.4(298) | 79.5(271) | 82.7(282) | 73.6(251) | 76.3(260) |
| Mean ± Std. Dev. | 435 ± 89 | 100 (185 ± 146) | 115.2 ± 12.3 (199 ± | 114.6 ± 17.5 (208 ± | 110.5 ± 21.8 (195 ± | 108.7 ± 28 (191 ± | 105.1 ± 28.7 (193 ± | 107.4 ± 29 (188 ± | 103.8 ± 27.2 (190 ± | 96.8 ± 11.2 (172 ± |

TABLE 7-continued

Oral Administration of Carrier Complex in Diabetic (Streptozotocin Treated) Rats. (The amount of carrier complex is equal to that in complex insulin · SDS · TEA at 30 μ/kg without insulin.)

| # Rat | Bd. Wt. (g) | 0 (Initial Glucose mg/100 ml) | 15 | 30 | 45 | 60 | 90 | 120 | 180 | 300 |
|---|---|---|---|---|---|---|---|---|---|---|
| | | | 137) | 161) | 141) | 147) | 166) | 144) | 164) | 164) |

TABLE 8

Oral Administration of Albumin Complex of Albumin · SDS · TEA in a weight ratio of 5:75:3.6 in Diabetic (Streptozotocin Treated) Rats.

Glucose Level (% initial level) at Time Interval After Administration (min)

| # Rat | Bd. Wt. (g) | 0 (Initial Glucose mg/100 ml) | 15 | 30 | 45 | 60 | 90 | 120 | 180 | 300 |
|---|---|---|---|---|---|---|---|---|---|---|
| 253 | 441 | 100(85) | 114.1 (97) | 107.1 (91) | 91.8 (78) | 96.5 (82) | 112.9 (96) | 85.9 (73) | 80 (58) | 90.6 (77) |
| 254 | 489 | 100(103) | 107.8 (111) | 98.1 (101) | 67 (69) | 73.8 (76) | 65.1 (67) | 87.4 (90) | 109.7 (113) | 89.3 (92) |
| 255 | 579 | 100(91) | 118.7 (108) | 85.7 (78) | 85.7 (78) | 92.3 (84) | 84.6 (77) | 78.0 (71) | 86.8 (79) | 92.3 (84) |
| 261 | 464 | 100(281) | 89.3 (251) | 93.2 (262) | 99.6 (280) | 95.0 (267) | 103.2 (290) | 103.2 (290) | 104.3 (293) | 100 (282) |
| 278 | 294 | 100(391) | 111.8 (437) | 111.0 (434) | 103.1 (403) | 97.2 (380) | 96.4 (377) | 92.6 (362) | 99.5 (389) | 97.2 (377) |
| 281 | 274 | 100(664) | 96.4 (642) | 99.3 (659) | 96.4 (640) | 98.2 (652) | 100 (664) | 97.9 (650) | 100 (664) | |
| 282 | 309 | 100(331) | 110.6 (366) | 96.1 (318) | 102.4 (339) | 88.2 (292) | 105.4 (349) | 108.5 (359) | 101.8 (337) | 97.6 (323) |
| Mean ± Std. Dev. | 407.1 ± 116 | 100 (278 ± 211) | 106.9 ± 104 (287 ± 206) | 98.6 ± 8.5 (278 ± 215) | 92.3 ± 12.7 (270 ± 214) | 91.6 + 8.6 (262 ± 210) | 95.4 ± 15.9 (274 ± 218) | 93.4 ± 10.6 (271 ± 213) | 97.4 ± 10.4 (278 ± 214) | 94.5 ± 43 (205 ± 137) |

EXAMPLE 3

Four α-chloroethyl esters have been prepared and isolated purified in good yield; i.e., α-chloroethyl n-octanoate ($C_8$);

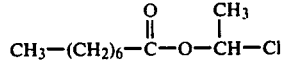

α-chloroethyl n-nonanoate ($C_9$);

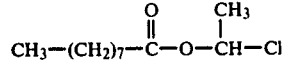

α-chloroethyl n-decanoate ($C_{10}$);

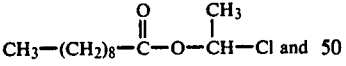

α-chloroethyl n-dodecanoate ($C_{12}$);

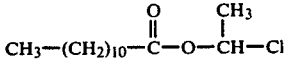

Two soft quaternary ammonium salts, [1-(n-dodecanoyloxy)ethyl]triethyl ammonium chloride (A) and [1-(n-dodecanoyloxy)ethyl]-3-methylimidazolium chloride (B), have been prepared by the method previously described in the specification. The toxicity of 1-methylimidazole is very slight (e.g., oral Mice LD$_{50}$, 1500 mg/kg; ipr. Mice LD$_{50}$, 380 mg/kg.)

1H NMR (CDCl$_3$) of ammonium ion (A): 6.6δ (quartet, 1H), 3.2δ (quartet, 6H), 2.3δ (triplet, 2H), 1.9δ (doublet 2H), 1.5δ (triplet, 9H), 1.3δ (broad singlet, 18H), 0.9δ (triplet, 3H).

$^1$H NMR (CDCl$_3$) of imidazonium ion (B): 10.3δ (singlet, 1H), 7.8δ (doublet, 2H), 7.2δ (quartet, 1H), 4.2δ (singlet, 3H), 2.4δ (triplet, 2H), 1.9δ (doublet, 3H), 1.4δ (broad singlet, 18H), 0.9δ (triplet, 3H).

The invention now being fully described, it will be apparent to one of ordinary skill in the art that many changes and modifications can be made thereto without departing from the spirit or scope of the invention as set forth herein.

What is claimed as new and desired to be secured by Letters Patent of the United States is:

1. An enterally effective, biologically active peptide or protein composition comprising:
a complex comprising a hydrophobic core complex of a biologically active peptide or protein complexed with an alkyl or alkenyl sulfate having 6-24 carbon atoms and 0-3 double bonds, said core complex forming an electrostatic complex with a soft quaternary ammonium ion of the formula $NR^1R^2R^3R^4$ wherein $R^1$ represents a $C_1$-$C_{12}$-alkyl group of substituted $C_1$-$C_{12}$ alkyl group said substituents being a hydroxyl group or an alkoxyl group of the formula —$OR^4$ where $R^4$ is an alkyl group having 1-4 carbon atoms;

$R^2$ and $R^3$ independently represent hydrogen, a $C_1$-$C_{12}$-alkyl group or a substituted $C_1$-$C_{12}$ alkyl group said substituents being a hydroxyl group or an alkyl group of the formula —$OR^4$ where $R^4$ is an alkyl group having 1-4 carbon atoms; and $R^4$ represents hydrogen or a radical of the formula

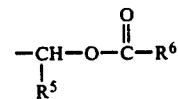

wherein $R^5$ is hydrogen, $C_1$-$C_5$ n-alkyl group and $R^6$ is a linear alkyl or alkenyl group having a 6-22 carbon atoms and 0-3 double bonds; or $R^1$ and $R^2$ together represent a divalent radical or the formula $-CH_2CH_2CH_2CH_2-$, $-CH_2CH_2CH_2CH_2CH_2-$, $-CH=CH-N=CH-$, or $-CH_2CH_2OCH_2CH_2-$;

with the proviso that when $R^1$ and $R^2$ together represent a divalent radical, said radical may be substituted by hydroxyl, $R^1$, or $-OR^4$; and that when $R^2$ is hydrogen, $R^1$ is not methyl.

2. The composition of claim 1, wherein said sulfate is an alkyl sulfate.

3. The composition of claim 2, wherein said alkyl sulfate contains from 10 to 14 carbon atoms.

4. The composition of claim 2, wherein said alkyl sulfate is dodecyl sulfate.

5. The composition of claim 1, wherein said soft quaternary ammonium ion is a protonated trialkylamine containing from 6 to 10 total carbon atoms.

6. The composition of claim 5, therein said trialkylamine contains 6 total carbon atoms.

7. The composition of claim 6, wherein said trialkylamine is triethylamine.

8. The composition of claim 1, wherein the ratio of said alkyl sulfate to said quaternary ammonium ion is a 1:1 molar ratio.

9. The composition of claim 1, wherein said peptide or protein is present in a weight ratio of about 1:0.4 with respect to said alkyl or alkenyl sulfate.

10. The composition of claim 1, wherein said peptide or protein is present in a weight ratio of about 1:1.4 with respect to said alkyl or alkenyl sulfate.

11. The composition of claim 2, wherein said biologically active peptide or protein is a peptide hormone.

12. The composition of claim 11, wherein said hormone has a molecular weight of less than 7000.

13. The composition of claim 2, wherein said peptide or protein is insulin.

14. The composition of claim 13, wherein said alkyl sulfate contains 10, 12 or 14 carbon atoms.

15. The composition of claim 14, wherein said alkylsulfate is dodecyl sulfate.

16. The composition of claim 15, wherein the weight ratio of insulin to dodecyl sulfate is about 1:1.4.

17. The composition of claim 13, wherein the weight ratio of insulin to dodecyl sulfate is about 1:0.4.

18. The composition of claim 16, wherein said quaternary ammonium ion is present in a 1:1 molar ratio to said alkyl sulfate.

19. The composition of claim 18, wherein said soft quaternary ammonium ion is protonated triethylamine.

20. A pharmaceutical composition, comprising: the sandwich complex of claim 1 and a pharmaceutically acceptable carrier.

21. The composition of claim 20, wherein said carrier is water or an aqueous solution of a non-toxic salt.

22. The composition of claim 20, wherein said carrier is a dilute aqueous solution of a mineral acid having a pH of less than 4.

23. The composition of claim 22, wherein said carrier is 0.005 M phosphoric acid.

24. The composition of claim 20, wherein said complex is lyophilized and said carrier is a solid.

25. A method of treating diabetes comprising enterally administering to a diabetic human or animal an amount of the sandwich complex of claim 13 sufficient to produce a hypoglycemic effect.

26. A method of treating diabetes comprising enterally administering to a diabetic human or animal an amount of the sandwich complex of claim 19 sufficient to produce a hypoglycemic effect.

27. The method of claim 25, wherein said administering is orally administering.

28. The method of claim 26, wherein said administering is orally administering.

29. A method of producing an enterally effective, biologically active peptide or protein composition, comprising the steps of:

dissolving a biologically active peptide or protein in an aqueous solvent to form a solution;

adding an alkyl or alkenyl sulfate having 6-24 carbon atoms and 0-3 double bonds to said solution to form a hydrophobic core complex;

adding a soft quaternary ammonium ion to the solution of said core complex, wherein said ammonium ion has the formula $NR^1R^2R^3R^4$ wherein $R^1$ represents a $C_1$-$C_{12}$-alkyl group or a substituted $C_1$-$C_{12}$ alkyl group said substituents being a hydroxyl group or an alkoxyl group of the formula $-OR^4$ where $R^4$ is an alkyl group having 1-4 carbon atoms;

$R^2$ and $R^3$ independently represent hydrogen, a $C_1$-$C_{12}$-alkyl group, or a substituted $C_1$-$C_{12}$ alkyl group said substituents being a hydroxyl group or an alkoxyl group to the formula $-OR^4$ where $R^4$ is and alkyl group having 1-4 carbon atoms; and $R^4$ represents hydrogen or a radical of the formula $$-\underset{\underset{R^5}{|}}{CH}-O-\overset{\overset{O}{\|}}{C}-R^6$$

where $R^5$ is hydrogen or $C_1$-$C_5$ n-alkyl group and $R^6$ is a linear alkyl or alkenyl group having 6-22 carbon atoms and 0-3 double bonds; or $R^1$ and $R^2$ together represent a divalent radical of the formula $-CH_2CH_2CH_2CH_2-$, $-CH_2CH_2CH_2CH_2CH_2-$, $-CH=CH-N=CH$, or $-CH_2CH_2OCH_2CH_2-$;

with the proviso that when $R^1$ and $R^2$ together represent a divalent radical, said radical may be substituted by hydroxyl, $R^1$, of $-OR^4$ and that when $R^2$ is hydrogen, $R^1$ is not methyl;

thereby forming a complex comprising said hydrophobic core complex in an electrostatic complex with said ammonium ion.

30. The method of claim 29, wherein said sulfate is an alkyl sulfate.

31. The method of claim 30, wherein said sulfate is dodecyl sulfate.

32. The method of claim 29, wherein said soft quaternary ammonium ion is a protonated trialkyl amine.

33. The method of claim 32, wherein said amine is triethylamine.

34. The method of claim 29, wherein said peptide or protein is a peptide hormone.

35. The method of claim 34, wherein said hormone is insulin.

36. The method of claim 29, wherein said sulfate is dodecyl sulfate, said soft quaternary ammonium ion is a trialkylamine, and said peptide or protein is insulin.

* * * * *

UNITED STATES PATENT AND TRADEMARK OFFICE
CERTIFICATE OF CORRECTION

PATENT NO. : 4,582,820
DATED : April 15, 1986
INVENTOR(S) : Lin-nar L. Teng

It is certified that error appears in the above-identified patent and that said Letters Patent is hereby corrected as shown below:

Column 1, line 4, before BACKGROUND OF THE INVENTION, insert the following: --"This invention was made with government support under grant number R01 HL 22035 awarded by the National Institutes of Health. The Government has certain rights in the invention."--

Signed and Sealed this

Fifth Day of October, 1993

Attest:

BRUCE LEHMAN

Attesting Officer

Commissioner of Patents and Trademarks